United States Patent [19]

Giammara et al.

[11] Patent Number: 4,690,901
[45] Date of Patent: Sep. 1, 1987

[54] SILVER METHENAMINE STAINING METHOD

[75] Inventors: Beverly L. Giammara; Jacob S. Hanker, both of Chapel Hill, N.C.

[73] Assignees: The University of North Carolina at Chapel Hill, Chapel Hill; Microelectronics Center of North Carolina, Research Triangle Park, both of N.C.

[21] Appl. No.: 574,108

[22] Filed: Jan. 26, 1984

[51] Int. Cl.$^4$ ................. G01N 21/75; G01N 33/52
[52] U.S. Cl. ........................................ 436/86; 424/3; 436/63; 436/87; 436/94; 436/164
[58] Field of Search .............. 436/63, 94, 164, 86, 436/87; 356/36; 424/3

[56] References Cited

U.S. PATENT DOCUMENTS 4,296,201 10/1981 Ax et al. .................................. 435/7

FOREIGN PATENT DOCUMENTS 0974201 11/1982 U.S.S.R. .................................. 424/3

OTHER PUBLICATIONS

Merril et al., Anal. Biochem., vol. 110, No. 1, pp. 201–207, 1981.
Grocott, Am. J. Clin. Path., vol. 25, pp. 975–979, 1955.
Thiery, Chemical Abstract 68: 112091R, 1968.
Kohler, Chem. Abs., 94: 135465s, 1981.
Burr, Chem. Abs., 77: 45161;, 1972.
Harada, Chem. Abs., 93: 110148g, 1980.
Burr, Chem. Abs., 79: 15460e, 1973.
Berger et al, Chem. Abs. 79: 89920b, 1973.
Sedar et al, Chem. Abs., 80: 142697h, 1974.
Dutt, Chem. Abs., 91: 206787z, 1979.
Dutt, Chemical Abstract, 90: 117461a, 1978.
Courtoy et al, Chem. Abs., 88: 148459u, 1978.
Arnold M. Seligman, Hannah L. Wasserkrug and Jacob S. Hanker, "A New Staining Method (OTO) for Enhancing Contrast of Lipid-Containing Membranes and Droplets in Osmium Tetroxide-Fixed Tissue with Osmiophilic Thiocarbohydrazide (TCH)", reprinted from The Journal of Cell Biology, 1966, vol. 30, No. 2. pp. 424–432.
Jacob S. Hanker, Chandicharan Deb, Hannah L. Wasserkrug and Arnold M. Seligman, "Staining Tissue for Light and Electron Microscopy by Bridging Metals with Multidentate Ligands", reprinted from Science, Jun. 17, 1966, vol. 152, No.1 3729, pp. 1631–1634.
Hanker et al, "Osmiophilic Reagents: New Cytochemical Principle for Light and Electron Microscopy"–Science–Nov. 20, 1964 vol. 146, No. 3647, pp. 1039–1043.
"Histochemical Demonstration of Some Oxidized Macromolecules with Thiocarbohydrazide (TCH) or Thiosemicarbazide (TSC) and Osmium Tetroxide," The Journal of Histochemistry and Cytochemistry, 1965, Seligman and Hanker.
"Importance of Controls for the Demonstration of Carbohydrates in Electron Microscopy with the Silver Methenamine or the Thiocarbohydrazide-Silver Proteinate Methods",–Aug. 1, 1973, R. Courtoy.
"Mise en Evidence des Polysaccharides sur Coupes Fines en Microscopie Electronique," (1967) Thiery-J. Microscopie (1967), 6, 987–1018.
"New Electron Opaque and Conductive Stains for Basement Membranes", AADR Abstracts–1983–B. Giammara, T. Romaine, and J. Hanker.

Primary Examiner—Michael S. Marcus
Assistant Examiner—Robert J. Hill, Jr.
Attorney, Agent, or Firm—Cushman, Darby & Darby

[57] ABSTRACT

A staining technique for specimens which involves the sequential treatment of specimens with periodic or hydrochloric acid, thiocarbohydrazide or thiosemicarbazide, and silver methenamine. The technique, when using periodic acid, provides an excellent stain to evaluate glycomacromolecules and fibrovascular tissue and to conduct a broad spectrum of staining procedures for all modes of microscopy. Use of hydrochloric acid facilitates evaluation of cell nuclear DNA and chromatin.

9 Claims, No Drawings

SILVER METHENAMINE STAINING METHOD

The invention was made in connection with work sponsored by the United States Navy Medical Research & Development Command under ONR Contract N00014-82-K-0305.

BACKGROUND AND SUMMARY OF THE INVENTION

The present invention relates to staining techniques for biological specimens which provide for excellent visual clarity and contrast in the stained specimen.

While a variety of stains are available for either light or electron microscopy of glycomacromolecules, such as glycogen, glycoproteins, reticular fibers basement membranes, and nuclear DNA there is a need for a stain that works well for both of the various modes of microscopy.

The use of periodic acid or hydrochloric acid in conjunction with a Schiff reagent are known staining procedure, but does not provide as high a degree of contrast and clarity as one would desire.

Accordingly, it is the primary object of the present invention to provide a procedure for the staining of biological specimens which result in a high degree of visual clarity and contrast in the stained specimen.

This and other objects of the invention will become more apparent from the discussion which follows.

Generally speaking, the present invention provides a procedure for the staining of a biological or other specimen by contacting the specimen sequentially with periodic or hydrochloric acid, thiocarbohydrazide or thiosemicarbazide, and silver methenamine.

DETAILED DESCRIPTION OF THE INVENTION

More specifically, the staining procedure of the present invention comprises the following sequential steps:
(a) contacting the specimen with periodic acid or hydrochloric acid;
(b) rinsing the specimen in water;
(c) contacting the rinsed specimen with an acetic acid solution of thiocarbohydrazide or thiosemicarbazide;
(d) rinsing the specimen in distilled water;
(e) contacting the specimen with an ammoniacal solution of silver methenamine; and
(f) rinsing the specimen.

Optionally, one may further treat the stained specimen by immersing it in glycerin diluted formalin, or other reducing agents.

The choice of periodic or hydrochloric acid in the initial stage depends upon the features one wishes to observe. Thus, in evaluating fibrovascular tissue and glycogen macromolecular structures the use of periodic acid is dictated at ambient temperatures. In the instances where one wants to observe the DNA structure such as cell nuclei or chromatin, hydrochloric acid is recommended, and treatment should take place at an elevated temperature suitably in the range of ambient to about 60° C. Acid concentrations of from about 0.5 to 3 percent w/v, and preferably about 1 percent may be employed. Treatment time may vary widely from about 10 minutes to as much as two hours, but generally about 10 to 15 minutes is sufficient.

Treatment with thiocarbohydrazide or thiosemicarbazide (preferably thiocarbohydrazide) may suitably be carried out at concentrations of about 0.2 to about 0.5 percent w/v or greater in either a 10 to 30 percent v/v (preferably about 20%) acetic acid solution. In instances where one wishes to observe nuclear chromatin or DNA, these substances may simply be dissolved in water. The time of this treatment is not critical and may vary from as short as ten minutes to as long as 24 hours, but generally about 15 minutes is sufficient at room temperature. Subsequent to this treatment the specimen should be thoroughly rinsed in distilled water.

Treatment with silver methenamine may be carried out at a concentration ranging from as low as 0.5% to 10% w/v or greater. Preferred concentrations are about 1%. The silver methenamine is dissolved in a weakly (less than 1% v/v ammonia) ammoniacal solution. Treatment time may vary widely, but sould be for a sufficient period to allow for reduction of the silver methenamine. Generally, periods of from as short as five minutes to as long as 24 hours may be used. Reduction of the silver methenamine may be induced by the use of ultra-violet light, application of heat, and/or the application of a reducing agent such as formaldehyde, sodium bisulfite or sodium thiosulfate after the silver methenamine treatment. As will be appreciated, the present procedure is applicable to a wide variety of biological speciments including, inter alia, glycogen, reticular fibers, basement membranes and for detection of bacterial endotoxins, nuclei of any cell nucleolar organizer of malignent cells, bacterial and cellular DNA and chromatin.

The following examples are offered to more fully illustrate the present invention, but are not to be construed as limiting the scope thereof.

The silver methenamine which is employed advantageously is prepared by dissolving eight grams of silver nitrate in 100 ml of distilled water. Twenty-five grams of methenamine is dissolved in 100 ml of distilled water. The silver nitrate solution is then added to the methenamine solution at room temperature with stirring to form the desired silver methenamine precipitate. The precipitate is vacuum filtered, air dried, washed with ether, and air dried again. The dried material is then ground to a powder in a mortar and pestle and stored under refrigeration in the dark until use.

The resulting silver methenamine compound is a very stable powder and will go into solution easily. As will be appreciated the procedure described does not require the use of heat or lengthy reducing procedures.

EXAMPLE ONE

Mandibular rami from sacrificed rats were fixed, decalcified and sectioned. The sectional specimens were treated in 1% periodic acid for thirty minutes and then rinsed with distilled water. The specimens were then treated for 15 minutes with a 20% acetic acid solution having 0.2% thiocarbohydrazide dissolved therein. The specimens were again rinsed in distilled water and immersed in an ammonical aqueous 1% silver methenamine solution under a UV lamp for 15 minutes. The specimens were then rinsed in distilled water, allowed to stand in glycerine overnight and cover slipped.

The clarity and contrast of the stained section so treated are excellent for observing capillary sprouts, endotheial cells, fibroblasts and connective tissue fibers.

EXAMPLE TWO

Portions of tissues were fixed in 4% formaldehyde, 1% glutaraldehyde 0.1 M in either phosphate or cacodylate buffer (pH 7.4) for 2-3 hours. After rising in buffer for 3 hours to overnight, Vibratome sections were made. Sections were stored in the same buffer until the PATS reaction was run using the following procedure:

1. Immerse in freshly prepared 2% ferric chloride for 10 min followed by three rinses in distilled water, 2 min. each.
2. Immerse in freshly prepared 1% periodic acid for 30 min. followed by three rinses in distilled water, 2 min. each.
3. Immerse in freshly prepared 0.2 thiocarbohydrazide (TCH) in 20% acetic acid for 15 min. followed by six rinses in distilled water, 2 min. each.
4. Immerse in 1% ammoniacal silver methenamine solution.

This solution was prepared by dissolving 100 mg in 10 ml distilled water containing 100 microliters concentrated ammonium hydroxide (ACS) and can be kept in the refrigerator for months. Sections placed in a glass Petri dish are exposed to an ultraviolet lamp for 15 min. The sections are rinsed in at least 2 changes of distilled water and then covered with glycerin.

Sections mounted with glycerin on glass slides can be peviewed by light microscopy prior to embedment. The reticular fiber staining develops in glycerin generally from 1-12 hours at room temperature. After development in glycerin the coverglass is then removed and the sections are rinsed with dilute alcohol followed by stepwise dehydration in the usual manner for electron microscopy and embedment is epoxy.

EXAMPLE THREE

For the demonstration of neuclear DNA, Chromatin, or neuclearprotein, the procedure of Example Two is modified by merely deleting Step 1 and substituting 1N HCl for periodic acid and treating at a temperature of 60° C. for ten minutes.

It should be appreciated that the procedure of the present invention is applicable to a broad spectrum of biological staining procedures including, but certainly not limited to light microscopy, frozen sections, paraffin sections, plastic sections and epoxy sections. Included as well are all types of biological procedures for electronmicroscopy, cryoultramircotomy, immunolabeling procedures, scanning and backscattered electron imaging and other modes of electron microscopy. In addition, semiconductors or photoresists may be suitably stained.

Stained specimens resulting from the present procedure may be characterized not only by their excellent visual contrasts, but their electroconductive nature. The stained specimens are electrically conductive (due to the presence of silver ions) and sufficiently electron dense to be suitable for conductivity purposes, for viewing by light microscopy and various modes of electron microscopy, as well as for X-ray analysis.

The invention having been thus described, it will be appreciated that various modifications can be applied thereto without departing from the scope of the claims which follow. Furthermore, the invention may comprise, consist, or consist essentially of the steps and materials recited herein.

We claim:

1. A procedure for staining a biological specimen comprising the steps of
   (a) contacting a biological specimen with a solution containing periodic acid or hydrochloric acid;
   (b) contacting the specimen of step (a) with a solution containing thiocarbohydrazide or thiosemicarbazide; and
   (c) contacting the specimen of the step (b) with a solution of silver methenamine resulting in a stained specimen wherein silver methenamine is synthesized by mixing aqueous solutions containing silver nitrate and methenamine, filtering a resulting silver methenamine precipitate solid and air drying said solid.

2. The procedure according to claim 1 wherein prior to step (a), said biological specimen is fixed in a buffer solution containing formaldehyde and glutaraldehyde.

3. The procedure of claim 1 wherein the biological specimen consists of deoxyribonucleic acids or nuclear-proteins.

4. The procedure according to claim 1, wherein the specimen is rinsed in water between steps (a) and (b) and between steps (b) and (c), the solution of silver methenamnine in step (c) is an ammonical solution, and the specimen is rinsed in water after step (c).

5. The procedure of claim 4 further comprising the step of immersing said rinsed specimen obtained in the last step of said procedure in glycerine diluted formalin.

6. The procedure of claim 4 wherein step (c) is carried out while exposing said specimen to ultra-violet light.

7. The procedure of claim 4 wherein step (c) is carried out while subjecting said specimen to ultra-violet light, heat, a reducing agent or a combination thereof.

8. The procedure of claim 4 wherein a solution containing about 0.5 to 3 percent w/v periodic acid is employed in step (a), a solution containing about 0.2 to 0.5 percent w/v thiocarbohydrazide or thiosemicarbazide in a 10 to 30 percent v/v solution of acetic acid is employed in step (b), and an ammonical solution containing 0.5 to 10 percent w/v silver methenamine in an aqueous solution of less than 1 percent v/v ammonia in water is employed in step (c).

9. The procedure of claim 8 wherein step (b) is carried out using a solution containing thiocarbohydrazide.

* * * * *